United States Patent [19]

Darrow

[11] Patent Number: 4,788,183

[45] Date of Patent: Nov. 29, 1988

[54] METHOD FOR TREATMENT OF DYSLIPIDEMIA IN HUMANS

[75] Inventor: William Darrow, Basking Ridge, N.J.

[73] Assignee: Schering Corporation, Kenilworth, N.J.

[21] Appl. No.: 126,441

[22] Filed: Nov. 30, 1987

[51] Int. Cl.$^4$ ............................................. A61K 31/615
[52] U.S. Cl. ..................................... 514/166; 514/824
[58] Field of Search ................................. 514/166, 824

[56] References Cited

U.S. PATENT DOCUMENTS 4,012,444  3/1977  Lunts et al. ........................... 544/162
4,658,060  4/1987  Gold et al. ............................ 564/165

FOREIGN PATENT DOCUMENTS 79103473.9  4/1980  European Pat. Off.

Primary Examiner—Albert T. Myers
Assistant Examiner—Raymond J. Henley, III
Attorney, Agent, or Firm—Stephen I. Miller

[57] ABSTRACT

A method for treating dyslipidemia in a human is disclosed, the dyslipidemia is characterized by an HDL serum cholesterol level of below about 50 milligrams per deciliter. The method consists of the administration to said human of a therapeutically effective amount of 5-{(R)-1-hydroxy-2-[(R)-(1-methyl-3-phenylpropy)amino]-ethyl}salicylamide, 5-{(S)-1-hydroxy-2-[(R)-(1-methyl-3- phenylpropyl)amino]ethyl}salicylamide or a pharmaceutically acceptable salt thereof or a mixture thereof.

10 Claims, No Drawings

METHOD FOR TREATMENT OF DYSLIPIDEMIA IN HUMANS

This invention relates to a method for treatment of dyslipidemia in humans by administering a therapeutically effective amount of the S,R or R,R isomer of 5-{1-hydroxy-2-[(1-methyl-3-phenylpropyl)amino]ethyl}-salicylamide, a pharmaceutically acceptable salt thereof or a mixture of such compounds. The invention also relates to the use of these compounds for the preparation of pharmaceutical compositions useful in treatment of dyslipidemia. The dyslipidemia referred to herein is characterized by an HDL cholesterol blood level concentration of less than 50 mg/dl. While no definite guidelines are available for levels of HDL cholesterol, the study group of the European Atheroscelerosis Society has provisionally set a cutoff point of 35 mg/dl for the lower limit of plasma HDL [Eur. Heart J., 8, 77 (1987)]. Also, there is growing evidence of the protective role of HDL cholesterol in atherogenesis [N. Eng. J. Med., 317, 1237 (1987)]. Thus, agents which increase the HDL cholesterol level with a resultant increase in HDL/LDL and HDL/total cholesterol ratios would be valuable for treatment of dyslipidemia characterized by a low level of HDL cholesterol.

When used herein, the term therapeutically effective amount means a sufficient amount of 5-{(R)-1-hydroxy-2-[(R)-(1-methyl-3-phenylpropyl)amino]ethyl}-salicylamide, 5-{(S)-1-hydroxy-2-[(R)-(1-methyl-3-phenylpropyl)amino]ethyl}salicylamide or a pharmaceutically acceptable salt thereof as well as mixtures thereof to effect an increase in the HDL cholesterol level of a human, said human having a pretreatment HDL cholesterol plasma level of below about 50 mg/dl.

The compound 5-{1-hydroxy-2-[(1-methyl-3-phenylpropyl)amino]ethyl}salicylamide is known in the art (see for example U.S. Pat. No. 4,012,444) and is a mixture of four isomers. The individual isomers may be separated or produced by methods known to those skilled in the art. For example the preparation of the R,R-isomer is described in U.S. Pat. No. 4,658,060. The compounds are known to have an antihypertensive effect.

It has now surprisingly been found that the compounds are also useful in the treatment of dyslipidemia characterized by HDL serum cholesterol levels of about 50 mg/dl and below. The method of the present invention may be practiced with hypertensive, hypotensive and normotensive individuals.

EXAMPLE

A group of patients (27) having HDL cholesterol levels below 35 mg/dl (average 31 mg/dl) was treated with the R,R-isomer described above at dosages ranging from 200 to 1600 mg/day (average dose 750 mg/day) and were evaluated for their HDL cholesterol level. At the end of one year the average increase of the HDL level was about 9 mg/dl which represents a 47% increase in the HDL/LDL ratio. The increase in HDL/total cholesterol ratio was about 26%.

Another group of 45 patients having pretreatment HDL levels between 35 and 50 mg/dl was subjected to the same treatment. At the end of one year the HDL level had increased by about 1.7 mg/dl which represents an 18% increase in the HDL/LDL ratio. The increase in the HDL/total cholesterol ratio was about 5.7%.

Suitable pharmaceutically acceptable acids for preparing the pharmaceutically acceptable salts of the S,R and R,R isomers are for example hydrochloric, sulfuric, phosphoric, benzoic, acetic, citric and the like. The preferred salt is the hydrochloride and the preferred isomer of the invention is the R,R isomer. The salts are prepared by methods known to those skilled in the art.

The compounds of the invention are preferably administered orally but can also be administered by injection or other convenient route. The effective oral dose for example for the (R,R) isomer or a pharmaceutically acceptable salt thereof will typically lie within the range of 50 to about 1600 mg/day, preferably from about 100 to about 1000 mg/day.

The invention therefore provides pharmaceutical compositions containing as active ingredient the R,R and/or S,R isomers of 5-{1-hydroxy-2-[(1-methyl-3-phenylpropyl)amino]ethyl}salicylamide or a pharmaceutically acceptable acid addition salt thereof, together with a pharmaceutical carrier or excipient. The compositions are preferably in the form of dosage units, e.g. tablets, pills, capsules, suppositories or injectable preparations in ampoules. The compositions may also be for example in the form of powders, syrups, solutions, elixirs or suspensions.

The required daily dosage may be administered in single or divided doses. The exact dose to be administered will, of course, be dependent upon various factors such as the age and weight of the subject, the severity of the dyslipidemia being treated and the individual response. By observing the various factors, one skilled in the art will be able to modify the daily dosage requirement and ascertain the optimum dosage level for each subject.

Dosage units preferably contain from 2 to 500 mg., more preferably from 10 to 200 mg., of the isomer according to the invention (or pharmaceutically acceptable acid addition salt thereof).

Typical pharmaceutically acceptable carriers for use in formulations described above are exemplified by: sugars such as lactose, sucrose, mannitol and sorbitol; starches such as corn starch, tapioca starch and potato starch; cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; vegetable oils such as peanut oil, cottonseed oil, sesame oil, olive oil and corn oil; non-ionic, cationic and anionic surfactants; ethylene glycol polymers; fatty alcohols; hydrolyzed cereal solids; and other non-toxic compatible fillers, binders, disintegrants, and lubricants commonly used in pharmaceutical formulations.

PHARMACEUTICAL FORMULATIONS

In the following examples, the active ingredient is preferably 5-{(R)-1-hydroxy-2-[(R)-(1-methyl-3-phenyl-propyl)amino]ethyl}salicylamide hydrochloride, but an equivalent quantity of the (R,R) isomer itself or of another pharmaceutically acceptable acid addition salt, especially a salt named herein, may be substituted:

| Injectable Solution | mg/ml |
|---|---|
| Active ingredient | 5.00 |
| Methyl p-hydroxy benzoate | 0.80 |

| -continued | |
| --- | --- |
| Injectable Solution | mg/ml |
| Propyl p-hydroxybenzoate | 0.10 |
| Disodium Edetate | 0.10 |
| Citric Acid monohydrate | 0.08 |
| Dextrose | 40.00 |
| Water for injection qs ad | 1.00 ml |

MANUFACTURING PROCEDURE

Dissolve the p-hydroxybenzoates in a portion of water for injection at 60°–70° C., and cool the solution to 25°–35° C. Charge and dissolve all other excipients and the active ingredient. Bring the solution to final volume, filter it through a sterilizing membrane and fill into sterile containers.

| Oral Formulations: (a) Capsules: | | |
| --- | --- | --- |
| | Quantities per capsule | |
| Formula | (mg) | (mg) |
| Active ingredient | 200.0 | 100.0 |
| Lactose | 223.0 | 111.5 |
| Corn Starch | 75.0 | 37.5 |
| Magnesium Stearate | 2.0 | 1.0 |
| | 500.0 | 250.0 |

MANUFACTURING PROCEDURE

Blend the active ingredient, lactose and corn starch until uniform; then blend the magnesium stearate into the resulting powder. Encapsulate the mixture into suitably sized two-piece hard gelatin capsules.

| (b) Tablets | | |
| --- | --- | --- |
| | Quantities per tablet | |
| Formula | (mg) | (mg) |
| Active ingredient | 200.0 | 100.0 |
| Lactose | 211.0 | 105.5 |
| Corn Starch | 12.0 | 6.0 |
| Water (per thousand) | (120 ml)* | (60 ml)* |
| Corn Starch | 75.0 | 37.5 |
| Magnesium Stearate | 2.0 | 1.0 |
| | 500.0 | 250.0 |

*(The water evaporates during manufacture.)

MANUFACTURING PROCEDURE

Blend the active ingredient with the lactose until uniform. Blend the smaller quantity of corn starch with the water and add the resulting corn starch paste, then mix until a uniform wet mass is formed. Add the remaining corn starch to the resulting wet mass and mix until uniform granules are obtained. Screen the granules through a suitable milling machine, using a ¾″ stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

I claim:

1. A method for treating dyslipidemia in humans by administering a therapeutically effective amount of 5-{(S)-1-hydroxy-2-[(R)-(1-methyl-3-phenylpropyl)amino]-ethyl}salicylamide, 5-{(R)-1-hydroxy-2-[(R)-(1-methyl-3-phenylpropyl)amino]ethyl}salicylamide or a pharmaceutically acceptable salt thereof as well as a mixture thereof to a human in need thereof.

2. The method defined in claim 1 wherein the R,R isomer is administered in the form of its hydrochloride salt.

3. The method defined in claim 1 wherein said dyslipidemia is characterized by an HDL serum cholesterol level of less than about 50 mg/dl.

4. The method defined in claim 2 wherein said dyslipidemia is characterized by an HDL serum cholesterol level of less than about 50 mg/dl.

5. The method defined in claim 1 wherein the therapeutically effective amount is from about 50 to about 1600 mg/day in single or divided doses.

6. The method defined in claim 1 wherein the therapeutically effective amount is from about 100 to about 1000 mg/day in single or divided doses.

7. The method defined in claim 2 wherein the therapeutically effective amount is from about 100 to about 1000 mg/day in single or divided doses.

8. The method defined in claim 3 wherein the therapeutically effective amount is from about 100 to about 1000 mg/day in single or divided doses.

9. The method defined in claim 4 wherein the therapeutically effective amount is from about 100 to about 1000 mg/day in single or divided doses.

10. The method according to claim 1 wherein the therapeutically effective amount is administered orally.

* * * * *